United States Patent [19]

Ty

[11] 4,437,858

[45] Mar. 20, 1984

[54] SEPARATOR DISC AND HYPODERMIC SYRINGE INCORPORATING THE SAME AND METHOD

[76] Inventor: Perla J. Ty, 3640-B S. Main St., Santa Ana, Calif. 92707

[21] Appl. No.: 370,688

[22] Filed: Apr. 22, 1982

Related U.S. Application Data

[63] Continuation-in-part of Ser. No. 869,798, Jan. 16, 1978, abandoned.

[51] Int. Cl.³ .............................................. A61M 5/18
[52] U.S. Cl. ...................................................... 604/90
[58] Field of Search ....................... 604/89, 90, 91, 82, 604/150

[56] References Cited

U.S. PATENT DOCUMENTS

| | | | |
|---|---|---|---|
| 2,268,994 | 1/1942 | Smith | 604/91 |
| 3,494,359 | 2/1970 | Zackheim | 604/90 |
| 3,563,415 | 2/1971 | Ogle | 604/90 |
| 3,809,225 | 5/1974 | Coche | 604/90 |
| 4,254,768 | 3/1981 | Ty | 604/89 |

Primary Examiner—John D. Yasko
Attorney, Agent, or Firm—Beehler, Pavitt, Siegemund, Jagger & Martella

[57] ABSTRACT

A self-displacing separator disc is positioned transversely of a tubular member to form a seal in the bore of the member, which may be a hypodermic syringe, to provide two or more separate chambers containing material which is to be kept separated until use thereof. The separator disc is constructed to respond differentially to force or pressure on one side thereof by having peripheral regions of different frictional response with respect to the bore wall such that the disc is displaced out of a transverse orientation upon exposure to force or pressure. Various different structures of discs are described to achieve self-displacement of the disc in a bore which preferably has a uniform internal diameter along its effective length.

19 Claims, 12 Drawing Figures

U.S. Patent    Mar. 20, 1984    4,437,858
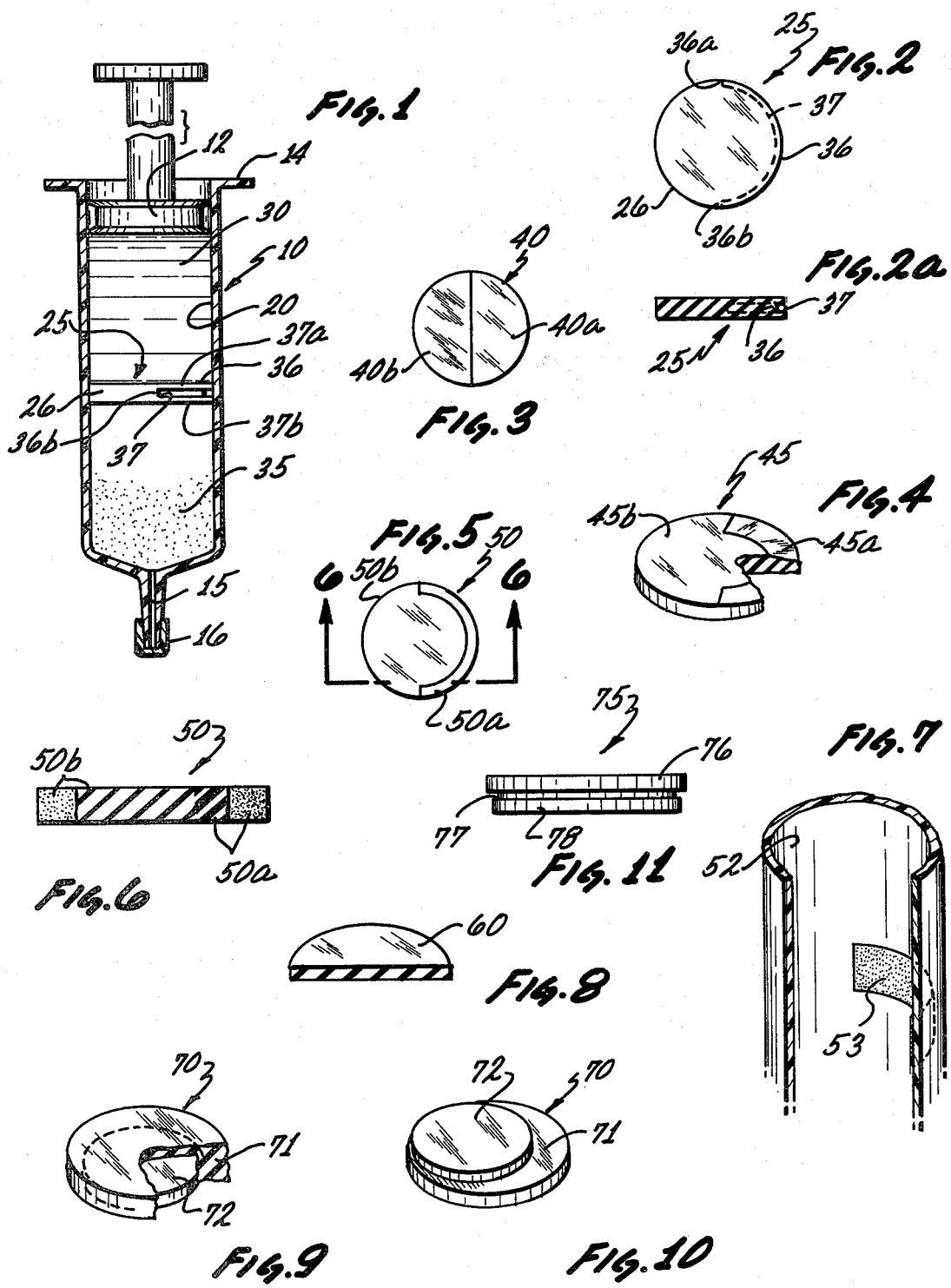

SEPARATOR DISC AND HYPODERMIC SYRINGE INCORPORATING THE SAME AND METHOD

RELATED INVENTIONS

This application is a continuation-in-part of Application Ser. No. 869,798, filed Jan. 16, 1978 now abandoned.

BACKGROUND OF THE INVENTION

1. Field of the Invention

This invention relates to separator discs for separating two or more materials in a tubular member, and more specifically, to an improved separator disc for separating materials in tubular members, as, for example, multicompartment tubular hypodermic syringes, and a method of operating the same.

2. Discussion of the Prior Art

Devices exist in the prior art in which tubular members contain separated different materials which are admixed prior to use. Separation of the materials is accomplished by a disc positioned transversely of a tubular member, which disc usually seals along the interior wall of the tubular member until such time as it is desired to intermix the two or more materials separated by the discs. Typical such devices are hypodermic syringes including at least one tubular barrel in which a disc is positioned in the barrel to separate components on each side of the disc.

There are numerous examples in prior patents of plural compartment members used to separate material by a disc. U.S. Pat. No. 2,610,628 of Sept. 16, 1972 describes a disc in the form of a gate plug held in place by seats, the diameter of the plug being less than the normal diameter of the tubular bore. U.S. Pat. No. 3,410,444 of Nov. 12, 1968 describes a container in which two hollow members are separated by a sleeve and plug arrangement. As the two members are moved axially towards each other, the plugs are unseated. U.S. Pat. No. 3,494,539 of Feb. 10, 1970 describes a two-compartment syringe in which a separator disc positioned transversely of the barrel is seated on a support member. Movement of the plunger causes the disc to tilt, thus forming a passageway between the chambers. U.S. Pat. No. 3,699,961 of Oct. 24, 1972 describes various forms of hypodermic syringes in which the plunger of the syringe is used to form two separate compartments. U.S. Pat. No. 3,908,225 of May 7, 1974 describes a container having two compartments separated by a disc. The disc is forced into a compartment of a larger diameter in order to effect mixing of the materials in the compartments. U.S. Pat. No. 3,842,836 of Oct. 22, 1974 is somewhat similar to the structure of U.S. Pat. No. 3,809,225. U.S. Pat. No. 4,113,098 of Sept. 12, 1978 describes a two-chamber ampule.

U.S. Pat. No. 3,494,359 discloses a structure in which two chambers are formed in a tubular barrel by a separator disc which rests on a support on the inside surface of the tubular barrel. The support functions as a cam for the separator to cock the separator out of a transverse orientation. In operation, a plunger must pass over the support on the inner side wall of the barrrel which forms the cam for the separator. For the plunger to accomplish its purpose, the plunger edge must have a close physical relationship to the inner wall of the barrel to form a seal. Thus, as the plunger comes into contact with the support on the inner side wall which forms the cam for the separator, an interference fit occurs which necessitates additional pressure and force on the plunger to overcome. When the syringe is being used in a pharmaceutical application for injection of materials into either human beings or animals by needle, the extra pressure and force which is instantaneously needed to overcome the interference of the support on the inner side wall of the barrel causes the entire syringe to deviate from its vertical and transverse orientation with respect to the subject being injected and thus may cause excess pain to be induced in the subject and may cause the materials being injected to be expressed in an area deeper within the subject than the user of the syringe had contemplated. At best, this may constitute a painful nuisance and at worst, the problem may constitute a dangerous set of circumstances with respect to the health and well-being of the subject being injected. In a nonpharmaceutical application of the syringe, the deviation in position of the syringe as the plunger is depressed may cause the materials being expressed out of the syringe to be applied other than where the user intends that the materials be applied.

As is apparent from the above discussion, the bulk of the prior devices use either seats on the bore of the panel to provide a band of localized reduced cross section as compared to the normal bore diameter, or involve separate chambers of different cross section. In these latter structures, the disc is positioned transversely of the bore having the smaller cross section and intermixing of the components involves forcing the disc into the chamber having the larger diameter.

In the case of hypodermic syringe, for example, the use of a band of reduced cross section is objectionable because the plunger must move freely and evenly in the bore. Where chambers of different diameters are used, this complicates plunger design since the plunger must seal during passage through the chamber of larger diameter.

It is thus apparent that a need exists for an effective manner of providing a separator disc in tubular members having essentially a uniform diameter along the length, without the necessity of utilizing localized areas of smaller diameter, or internal protrusions on the bore to effect displacement of the disc relative to the bore. Further, the use of bores of uniform diameter vastly simplifies manufacture of such tubular members, especially items such as hypodermic syringes.

SUMMARY OF THE INVENTION

One of the objects of this invention is to provide a separator disc which is capable of, among other things, being positioned transversely within a tubular member, such as the tubular barrel of a syringe, to form two or more separate chambers and which is capable of being displaced out of a transverse position by pressure and force conditions created on one side of the disc without the use of camming surfaces on the interior of the tubular member.

Other objects of this invention include an improved method of operating a multi-compartment syringe such that a separator disc may be used to form two or more separate chambers in a tubular member, the disc being in sealing engagement with the interior wall, and creating pressure and/or force conditions on one side of the disc to cause the latter to respond in a non-uniform manner which results in localized deflection of a portion of the periphery of the disc to enable passage of material from one chamber into another.

Still another object of this invention is to provide an improved apparatus for separately storing two components which are to be admixed prior to use. Typical such materials are resins and hardeners, pharmaceuticals, and the various materials described in U.S. Pat. No. 4,254,768, previously referred to, or the materials of the type set forth in the prior issued patents, by way of example.

Also an object of this invention is the provision of an improved separator disc for use as already described, in which the disc is constructed and arranged for controlled localized deflection without the need for an interior camming surface.

An important object of this invention is the provision of an assembly in the form of at least one tubular member, or an assemblage of two or more tubular members, in which the bore diameter of the tubular member or members is essentially of the same cross section and wherein a separator disc is positioned transversely of the bore, to form at least two separate chambers, such that movement of a plunger results in displacement of the disc for admixture of the components while allowing essentially smooth movement of the plunger through the bore or bores.

These and other objects are achieved in accordance with this invention by an improved separator disc and method, in which the disc is consturcted and arranged to respond differentially to forces or pressure on one side of the disc. Since the disc performs two functions, it is important to understand the environment in which the present invention is used.

One function of the disc is to form separate chambers in a tubular member. The separate chambers may contain a liquid or combination of liquids on one side, and a powder or admixture of powders on the other side, or liquids or a mixture of liquids on each side. The purpose of the separator disc is to maintain the components separated until immediately before use and then to permit easy and convenient mixing of the same and easy and convenient dispensing of the same. In the case of syringes, it is desired that dispensing be in a mode essentially the same as single barrel, single chamber syringes now in conventional use, i.e., the plunger should move smoothly through the barrel by the application of uniform pressure on the plunger.

Thus, the separator disc should form a seal with the wall of the tubular chamber, the disc being fabricated of a material which is inert with respect to the materials in the separated chambers. The various inert materials are themselves well known in the art. Since the disc must effectively seal to the wall, it is this quality of the disc which creates problems in mixing since the seal must be temporarily broken to permit material on one side of the disc to pass into the chamber on the other side of the disc. It is apparent that if movement of a plunger results only in uniform movement of all portions of the disc along the tubular barrel, i.e., the disc as a whole remains in a transverse plane, then no mixing can occur. It is for this reason that some of the prior devices which were hypodermic syringes used a cam surface on the interior wall to cause the disc to be displaced out of the transverse plane. However, in such a case, movement of the plunger over the cam tends to cause a jerky motion of the plunger which may have the objections noted.

By this invention several different, though simple, mechanisms may be used to achieve sealing of the disc to form two chambers while permitting the disc to be displaced without the need for an interior cam, while maintaining the advantage of a bore of essentially constant diameter. Thus, the present invention provides a system whereby the disc, or portion thereof, may respond differently to uniform pressure or force condicals on one side of the disc, and this maybe accomplished in any one of several different ways.

In one form of the invention, a disc of essentially uniform cross-sectional dimensions is used with a groove or other appropriate formation located along only a portion of the periphery while in sealing contact with the opposed wall. In effect, this arrangement, as well as others to be described, provides a structure in which the peripheral portion of the disc includes areas of differing frictional characteristics with respect to the wall with which the periphery of the disc is in engagement. In this form, the portion of the disc having the lower friction with respect to the wall will be displaced locally under pressure or force conditions created by the plunger such that a portion of the disc is displaced from the transverse position.

In another form, a portion of the periphery of the disc may be of a softer material than the remainder of the disc. In such a case the material of the disc may be the same or different, as will be explained.

In another form, the cross section of the disc may be such that a localized portion along the periphery is thinner than the balance of the disc to provide localized deflection.

Still another form involves a surface finish on the periphery of the disc which may, for example, be either smooth or roughened so that the periphery of the disc effectively possesses differential frictional characteristics with respect to the bore, thus permitting localized deflection in that area of least friction. Effectively, the same result may be achieved by providing a tubular bore in which a localized section of the bore provides different frictional qualities while the periphery of the disc is of a uniform surface quality. As a variant, the disc may be fabricated of different materials along various portions of the periphery to provide differential frictional qualities.

It is also within the teachings of this invention to use a disc of essentially uniform cross-sectional dimension and surface finish, with the cross section and diameter being in such a relation that non-uniform pressure or force conditions create localized flexing of a portion of the disc.

As is apparent from the above, the present invention may be used for products other than hypodermic syringes. For example, certain multi-component products should be kept separate until immediately before use, adhesives, potting compounds, lyophilizable materials, and the like which are not dispensed in a hypodermic syringe, but which may be mixed in a tubular member in which a plunger is used to disperse the mixed product. The present invention finds applicability with those types of products and basically any tubular dispenser including a plunger.

The above and other objects of the present invention will become readily apparent from the following detailed description.

BRIEF DESCRIPTION OF THE DRAWINGS

FIG. 1 is a view, partly in section and partly in elevation of one form of the present invention illustrating a separator disc in accordance with this invention positioned in a tubular member;

FIG. 2 is a plan view of the disc shown in FIG. 1;

FIG. 2a is a sectional view of an insert in accordance with this invention, somewhat similar to the disc of FIG. 2 and incorporating an insert in the peripheral groove;

FIG. 3 is a plan view of a disc for use in the present invention in which portions are of different hardness;

FIG. 4 is a view, partly in section and partly in elevation, showing another form of this invention in which the disc is of a non-uniform cross section;

FIG. 5 is a plan view of a disc for use in accordance with this invention in which the peripheral portion of the disc is of differing surface roughness;

FIG. 6 is a sectional view, partly in elevation and taken along the line 6—6 of FIG. 5;

FIG. 7 is a view, partly in section and partly in elevation, illustrating a form of the present invention in which the bore of the tubular member includes surface portions of differing roughness;

FIG. 8 is a view, partly in section and partly in elevation, of a disc in accordance with this invention in which the cross-sectional dimension is related to the diameter such that there is localized flexing of the disc;

FIG. 9 is a view partly in section and partly in elevation of a disc in accordance with this invention in which an insert is used to provide localized flexibility;

FIG. 10 is a view, partly in section and partly in elevation, of a disc in accordance with this invention in which a member is joined to another member in such a manner as to provide localized flexing; and FIG. 11 is a view in section of still another form of disc in accordance with this invention.

DETAILED DESCRIPTION OF THE INVENTION

Referring to the drawings, which illustrate a preferred form of the present invention, FIG. 1 shows a tubular member 10 which may be of plastic, glass or other suitable material. One end of the member 10 is open and receives a plunger 12, the lower end of which is in sealing relation to the interior bore or wall of the member 10.

The tubular member may include a flange 14 which cooperates with the plunger 12 to facilitate movement of the plunger relative to the member 10, it being understood that the flange may be located at any convenient place along the length of the member 10. The lower end of member 10 includes an outlet 15 covered by a cap 16 which may form a seal plug.

As illustrated, the bore 20 of the member 10 is of essentially a constant cross section and free of protrusions or areas of reduced diameter. Accordingly, the plunger 12, which is in sliding sealing relation with the bore 20, is capable of smooth passage through the bore without the jerky motion which might be encountered if the bore included an interior protrusion or a region of reduced bore diameter.

Positioned within the bore is a separator disc 25, arranged transversely of the bore, the disc 25 including a peripheral surface 26 which is in sealing engagement with the bore of the tubular member. The disc 25 effectively divides the tubular member into two chambers, 30 and 35, one on each side of the disc. Chambers 30 and 35 each include materials which are to be maintained separate from each other until admixed before use. The materials may be as described.

Referring now to FIGS. 1 and 2, the separator disc 25 includes a portion 36 of its periphery 26 which possesses different frictional qualities with respect to the bore 20 than does the balance of the periphery of the disc. In the form illustrated this may be accomplished by a groove 37 formed in the periphery of the disc part way along the circumference thereof. The groove may be semi-circular, V-shaped or U-shaped so as to form spaced peripheral lips 37a and 37b which contact the bore 20 for sealing engagement therewith.

The portion 36 of the periphery 26 of the disc 25 represents that segment of the periphery which has a lower friction with respect to the bore surface as compared to the balance of the periphery of the disc. The groove may include ends 36a and 36b which are sharp, i.e. terminate on the radius as shown, or may be tapered so as to change gradually and taper into the normal diameter of the disc. In the form illustrated, the groove 36 extends about 180° of the periphery, but may extend 270° or 300° depending upon the type of action desired during activation.

The disc may be fabricated of a variety of materials depending upon the environment in which it is used. Various fluorocarbon polymers may be used as well as polyethylene or other polyolefiln materials; polyethylene terephthalate may be used as well as the elastomers and polymers used in medical applications, e.g., medical grade silicone materials. A wide variety of materials may be used depending upon the contents of the chamber, shelf-life desired and the like, as is well known in the art.

In operation, assuming chamber 30 contains a liquid and chamber 35 a powder, as the plunger 12 is moved relative to the bore, any air in chamber 30 is compressed, and the liquid acts on the disc 25. Since the disc includes peripheral portions that frictionally respond differentially, the effect is to cause the portion of the disc having the lower friction with respect to the bore to unseat, i.e. the disc responds differentially to uniform force or pressure on one side thereof. Once the peripheral seal to the bore wall has been broken, fluid passes between bore wall and the deflected peripheral region of the disc for admixture with the contents of chamber 35. The differential frictional response of the disc results in the disc being displaced from a transverse orientation to one in which fluid flows past the disc into chamber 35.

The contents of chamber 35 may be dissolved by shaking and plug 16 may be removed and a needle attached. The mixed contents may now be dispensed by a smooth motion of the plunger through the bore, the face of the plunger ultimately contacting the upper face of the disc to urge it towards the outlet 15.

One of the unique advantages of the disc of the present invention is that it may be located axially along the bore at any point, thereby allowing formation of chambers 30 and 35 of different sizes as may be needed. In contrast to prior devices where the disc had to be located adjacent the protrusion or section of reduced diameter, the present invention provides some latitude in location of the disc axially in the bore.

In assembly, the powder charge is inserted, under aseptic conditions if necessary, the disc is inserted and located axially by use of a dummy plunger, or a standard plunger, the liquid is then charged, and a working plunger assembled to the unit.

While this invention has been described, for purposes of explanation, with respect to a single barrel syringe, it is understood that the invention may be used with a multiple barrel syringe, for example that described in U.S. Pat. No. 4,254,768.

A variant of the structure illustrated in FIGS. 1 and 2 includes placing in the peripheral groove an insert of material different from that of the disc in which case the grooved peripheral area with the peripheral insert would have either a higher or lower coefficient of friction than the remaining portion of the periphery. Such an arrangement will be illustrated in FIG. 2a in which insert 37 is located in recess 36 of the disc 25.

FIG. 3 illustrates a disc 40 structured to provide a differential response in which a portion 40a of the disc is fabricated of a material softer than the remaining portion 40b of the disc. Such a disc 40 may be used with a bore of uniform surface characteristics with the result that the disc 40 includes peripheral surface portions having differing frictional responses, with the resultant operation being that already described. While disc 40 is illustrated as being made up of a periphery of 180° of softer material, the softer material may be 270° or 300° of the periphery. The softer material may be of less than 180° of the periphery, if desired. In function and operation, the disc 40 performs as already described.

The differential frictional response may also be achieved by use of a disc 45 having a non-uniform cross-section in thickness, as shown in FIG. 4. In this form the cross-sectional thickness of the disc may become smaller in the direction radially outwardly of the center as illustrated in region 45a which is thinner than the remaining portion 45b. In this form a portion of the periphery of the disc is thinner in cross-section than the balance of the periphery, for example 180°, again to produce a differential frictional response along the periphery. The region of reduced cross-sectional thickness may be an annular band located along a region of the periphery of the disc, or may be semi-circular such that one half or more of the disc is of reduced cross-sectional thickness. Regardless of the precise form, the result is the same, the disc includes peripheral portions having different frictional characteristics with respect to the bore wall.

In another form, as illustrated in FIGS. 5 and 6, the disc 50 includes a peripheral wall portion 50a which is of a roughened texture as compared to peripheral wall portion 50b which is smooth. The body portion may be of uniform cross-sectional thickness. The peripheral wall 50b which is smooth possesses a lower frictional response than does peripheral wall portion 50b with the result that upon exposure to force or pressure, the disc responds differentially and is displaced from a transverse location in the bore. The disc may also be of non-uniform cross-sectional thickness such that the thickness in the region of the smooth periphery is less than that of the region of the roughened periphery.

Such a differential frictional response results in displacement of the disc relative to the bore, it is also possible in accordance with the present invention to provide a tubular member in which portions of the bore have different surface finishes to provide different frictional responses. Referring to FIG. 7, the bore 52 includes a band 53 which extends axially and circumferentially along the bore and which is of a rough surface finish as compared to the remaining portion of the bore. The bore has a uniform diameter, as described, and the roughened band may extend 60° to as much as 180° or more around the bore circumference. The disc may have a smooth peripheral surface and should be located axially in the bore so as to be in contact with the band 53.

In another form of the invention, as illustrated in FIG. 8, a disc is provided which is of uniform character throughout, i.e. hardness and surface finish. In this form, the ratio of the cross-sectional thickness and diameter have been coordinated and correlated to permit localized deflection of a portion of the disc, especially where the face of the disc is in contact with both a liquid and a gas. For example, using a standard high density polyethylene syringe whose inside diameter is between 0.710 to 0.715 inches, i.e., 0.712 inch average, a disc of a cross-section thickness between 0.135 to 0.141 inches and a diameter of 0.727 to 0.737 inches will result in movement of about 0.25 inches along the periphery of the disc thus allowing fluid to flow from the one chamber into the other.

FIG. 9 illustrates a form of disc 70 having a body portion 71 and an insert 72 placed non-symmetrically within the disc such that the periphery of the insert is located an uneven distance from the periphery of the body portion, resulting in a peripheral portion of the disc which responds differentially to pressure or force on the face of the disc. In this form, it is also possible to use an insert which is semi-circular and symmetrically located within the body. The insert may be completed encapsulated by the body portion to provide a peripheral portion which responds differentially. Rather than placing the insert 72 within the disc 70, it may be assembled on one surface of the body portion 71 of the disc as illustrated in FIG. 10.

In the form of illustrated in FIG. 11, the disc 75 may include a plurality of elements 76, 77 and 78. In this form, element 76 may be of 0.737 inch diameter for a tube of the diameter noted, and of 0.048 inch cross-section. Element 77 may be of 0.044 inch cross-section and smaller in diameter than each of 76 and 78. Element 78 may be of 0.048 inch cross-section and of 0.727 inch diameter. In this form the lower elements tend to support the upper element 76 which, being of comparatively thin material, tends to tilt easily. While element 77 is shown centered, it is understood that it may be non-symmetrical with respect to element 76.

It will be apparent from the foregoing description that various modifications and alterations may be made in accordance with the previously described structures and devices, without departing from the scope of the appended claims.

What is claimed is:

1. Apparatus for separately storing and admixing at least two materials, comprising:
   at least one tubular barrel means having an effective bore of essentially uniform diameter along the length thereof, a plunger at one end of said tubular barrel means adapted to be moved through said tubular barrel means,
   disc means positioned in said tubular barrel means and in sealing engagement with the wall thereof along the periphery of said disc and operative to divide said tubular barrel means into at least two separate chambers,
   said disc being so constructed and arranged as to be response to pressure and/or force conditions on one side thereof to form a communicating path between said chambers as a result of deflection of at least a portion of said disc away from said tubular barrel means, and
   said bore being essentially free of radially inwardly extending protrusions whereby said plunger may move freely and easily through said bore.

2. Apparatus as set forth in claim 1 wherein said disc includes peripheral portions having different frictional characteristics with respect to said bore.

3. Apparatus as set forth in claim 1 wherein the periphery of said disc includes groove means in a portion thereof.

4. Apparatus as set forth in claim 1 wherein a portion of the bore surface of said barrel in contact with the periphery of said disc is of a surface finish different from the remainder of said bore.

5. Apparatus as set forth in claim 1 wherein the ratio of the cross-section of the disc and the diameter thereof are coordinated and correlated to permit localized deflection thereof in response to pressure and/or force conditions on one side thereof.

6. Apparatus as set forth in claim 1 wherein said disc includes a body portion and an insert located non-symmetrically within said disc such that the periphery of said disc is located an uneven distance from the peripheral portion of said disc.

7. Apparatus as set forth in claim 1 wherein said disc includes a body portion and an insert positioned in overlying relation to said body portion.

8. Apparatus as set forth in claim 1 wherein said disc includes a plurality of elements the respective ratios of cross-section and diameter thereof being coordinated and correlated to permit deflection thereof in response to pressure and force.

9. Apparatus as set forth in claim 1 wherein said disc includes a portion along the periphery thereof of a cross-sectional thickness less than the remainder of said disc.

10. Apparatus as set forth in claim 1 wherein said disc includes peripheral portions having a rough surface finish as compared to other portions of the periphery.

11. Apparatus as set forth in claim 1 wherein said disc includes a peripheral portion which is softer than the balance of the peripheral portion of said disc.

12. Apparatus as set forth in claim 1 wherein said disc includes an insert therein which is of a hardness different from the balance of the material constituting said disc so as to provide peripheral surface portions which are relatively flexible.

13. Apparatus as set forth in claim 1 wherein said disc includes a body member of one hardness and an associated smaller diameter disc of a different hardness.

14. A self displacing separator disc for use in a tubular member having an effective bore of essentially uniform diameter along the length thereof for dividing said tubular member into at least two chambers comprising:

a relatively flat annular member proportioned to be received in sealing engagement with the bore of said tubular member, and said relatively flat circular member having the characteristics of being able to deflect locally along only a portion of the periphery thereof in response to pressure on one side thereof to provide for communication between the two chambers of the tubular member.

15. A self-displacing separator disc utilizing differentials of friction coefficients comprising:

a disc of solid material, the disc providing friction means along a portion of its edge causing one portion of the edge to have a coefficient of friction different than the coefficient of friction of the other portion of its edge.

16. A self-displacing separator disc utilizing differentials of friction coefficients of claim 15 wherein the friction means comprises a relieved channel along of the edge of the disc.

17. A self-displacing separator disc utilizing differentials of friction coefficients of claim 16 wherein the friction means comprises an insert of material along a portion of the edge of the disc having a different friction coefficient than the material of which the disc is constructed.

18. A self-displacing separator disc utilizing differentials of friction coefficients of claim 15 wherein the friction means comprises a portion of the edge of the disc being so constructed as to be less thick than the other portion of the edge of the disc.

19. A method for separately storing separated materials in a tubular structure having a smooth bore of essentially uniform diameter and being free of radially inwardly extending protrusions and including a plunger and wherein said separated materials are admixed prior to use, comprising the steps of:

positioning within the bore of said tubular structure a disc member so located as to separate at least two components in said tubular member, said disc member being in sealing engagement with the bore of said tubular member, and creating pressure and/or force conditions on one side of said disc to cause said disc to respond in a non-uniform manner to effect deflection of at least a portion of the periphery of said disc to enable passage of the material on one side of said disc to the other side of said disc for admixture with the material on the other side of said disc.

* * * * *